US011664112B2

(12) United States Patent
Huang et al.

(10) Patent No.: US 11,664,112 B2
(45) Date of Patent: May 30, 2023

(54) METHOD AND SYSTEM FOR TISSUE DENSITY ANALYSIS

(71) Applicant: SHANGHAI UNITED IMAGING HEALTHCARE CO., LTD., Shanghai (CN)

(72) Inventors: Shiquan Huang, Shanghai (CN); Changyun Qiu, Shanghai (CN); Weiwen Nie, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 382 days.

(21) Appl. No.: 16/729,601

(22) Filed: Dec. 30, 2019

(65) Prior Publication Data

US 2020/0135329 A1    Apr. 30, 2020

Related U.S. Application Data

(63) Continuation-in-part of application No. PCT/CN2017/091226, filed on Jun. 30, 2017.

(51) Int. Cl.
*G16H 30/20* (2018.01)
*G06T 7/136* (2017.01)
(Continued)

(52) U.S. Cl.
CPC ............. *G16H 30/20* (2018.01); *A61B 6/032* (2013.01); *A61B 6/463* (2013.01); *A61B 6/50* (2013.01);
(Continued)

(58) Field of Classification Search
None
See application file for complete search history.

(56) References Cited

U.S. PATENT DOCUMENTS 5,734,384 A * 3/1998 Yanof ................... G06T 17/10
345/419
5,978,696 A * 11/1999 VomLehn ............. A61B 34/20
600/416

(Continued)

FOREIGN PATENT DOCUMENTS

CN      1891155 A     1/2007
CN    101065065 A    10/2007
(Continued)

OTHER PUBLICATIONS

International Search Report in PCT/CN2017/091226 dated Apr. 12, 2018, 9 pages.
(Continued)

*Primary Examiner* — Michelle M Entezari
(74) *Attorney, Agent, or Firm* — Metis IP LLC

(57) ABSTRACT

The present disclosure provides a tissue density analysis system. The system includes an acquisition module configured to obtain image data and tissue density distribution data; a display module configured to display the obtained tissue density distribution data in one or more charts; a processing module configured to adjust the tissue density distribution data displayed in the one or more charts; and a storage module configured to store the image data, the tissue density distribution data and an instruction.

20 Claims, 10 Drawing Sheets

(51) Int. Cl.
  *A61B 6/03* (2006.01)
  *A61B 6/00* (2006.01)
  *G06T 7/00* (2017.01)
  *G06T 11/00* (2006.01)

(52) U.S. Cl.
  CPC .......... *A61B 6/5217* (2013.01); *G06T 7/0014* (2013.01); *G06T 7/136* (2017.01); *G06T 11/001* (2013.01); *G06T 11/008* (2013.01); *G06T 2207/10081* (2013.01); *G06T 2207/30096* (2013.01)

(56) References Cited

U.S. PATENT DOCUMENTS

| | | | |
|---|---|---|---|
| 6,198,797 B1 | 3/2001 | Majima et al. | |
| 6,711,433 B1* | 3/2004 | Geiger | G06T 11/008 378/98.12 |
| 10,140,421 B1* | 11/2018 | Bernard | G06V 10/764 |
| 2004/0101104 A1* | 5/2004 | Avinash | A61B 6/482 378/98.12 |
| 2005/0177790 A1* | 8/2005 | Molander | G06F 3/0482 715/700 |
| 2006/0164418 A1* | 7/2006 | Hao | G06T 11/206 345/440.2 |
| 2008/0195930 A1* | 8/2008 | Tolle | G06F 40/18 715/227 |
| 2010/0014729 A1* | 1/2010 | Choi | G06T 5/50 382/131 |
| 2010/0032165 A1* | 2/2010 | Bailey | G06F 30/00 703/2 |
| 2010/0074493 A1* | 3/2010 | Wiemker | G06T 7/0012 382/130 |
| 2010/0205007 A1* | 8/2010 | Meesa | G09B 23/286 707/E17.014 |
| 2011/0026800 A1 | 2/2011 | Tonomura et al. | |
| 2012/0108960 A1* | 5/2012 | Halmann | A61B 8/5292 715/810 |
| 2012/0207452 A1* | 8/2012 | Wang | G11B 27/034 386/E5.028 |
| 2014/0219416 A1 | 8/2014 | Kimoto et al. | |
| 2014/0321603 A1 | 10/2014 | Taguchi et al. | |
| 2015/0235085 A1 | 8/2015 | Goto | |
| 2015/0324536 A1 | 11/2015 | Shie et al. | |
| 2016/0040976 A1* | 2/2016 | Berkeley | G01N 21/01 356/479 |
| 2016/0171345 A1* | 6/2016 | Ragusa | G06K 9/6276 382/128 |
| 2017/0086766 A1 | 3/2017 | Mundry et al. | |
| 2017/0091935 A1* | 3/2017 | Leon | A61B 6/032 |
| 2018/0150992 A1* | 5/2018 | Lo | G06T 15/10 |

FOREIGN PATENT DOCUMENTS

| | | |
|---|---|---|
| CN | 101105862 A | 1/2008 |
| CN | 107392893 A | 11/2017 |
| JP | 2003102723 A | 4/2003 |

OTHER PUBLICATIONS

Written Opinion in PCT/CN2017/091226 dated Apr. 12, 2018, 8 pages.
Extended European Search Report in European Application No. 17916087.4 dated May 14, 2020, 7 pages.
Communication Pursuant to Article 94(3) EPC in European Application No. 17916087.4 dated Apr. 4, 2023, 8 pages.

* cited by examiner

METHOD AND SYSTEM FOR TISSUE DENSITY ANALYSIS

CROSS-REFERENCE TO RELATED APPLICATIONS

This application is a continuation-in-part application of International Application No. PCT/CN2017/091226 filed on Jun. 30, 2017, the entire contents of which are hereby incorporated by reference.

TECHNICAL FIELD

The present disclosure relates to a method and system for image display and processing, and in particular, relates to a tissue density analysis method and system.

BACKGROUND

With the development of modern computer technology and medical imaging technology, there is an ever-increasing demand for accuracy in the analysis of tissues or lesions in medical imaging. Density analysis based on computed tomography (CT) values has been widely used in the analysis of lesions, such as tumors and nodules, and in the analysis of lung tissues of emphysema patients. The CT value is a unit of measurement for determining the density of certain local tissues or organs in a human body. The CT value may quantitatively reflect an absorption rate of X-rays by tissues. When a tissue density analysis is performed, a user needs to divide a target tissue or lesion into multiple segments or multiple intervals according to the CT value, and evaluate the target tissue or lesion according to a proportion of a region corresponding to a CT interval or a CT segment in the target tissue.

SUMMARY

The tissue density analysis method provided by the present disclosure may present a CT value to a user in a relatively flexible and intuitive manner. Statistical results of a tissue density segment may be simultaneously displayed by using a histogram, a table, or the like, which may facilitate the user to operate the statistical results. The tissue density analysis system may improve the work efficiency of the user, and the display effect of the analysis results.

The present disclosure provides a tissue density analysis system. The system may include an acquisition module, a display module, a processing module, and a storage module. The acquisition module may be configured to obtain image data and tissue density distribution data. The display module may be configured to display the obtained tissue density distribution data in one or more charts. The processing module may be configured to adjust the tissue density distribution data displayed in the one or more charts. The storage module may be configured to store the tissue density distribution data and an instruction.

In some embodiments, the tissue density distribution data may be a CT value based on the medical image.

In some embodiments, adjusting the tissue density distribution data displayed in the one or more charts may include adjusting one or more tissue density segmentation thresholds.

In some embodiments, adjusting one or more tissue density segmentation thresholds may include modifying a tissue density segmentation threshold, adding a tissue density segmentation threshold, and/or deleting a tissue density segmentation threshold with annotation, click, double-click, or voice input.

In some embodiments, the processing module may be configured to simultaneously update the tissue density distribution data in the one or more charts according to the adjustment.

In some embodiments, the processing module may be configured to simultaneously update a color and/or data of a same density segmentation in the one or more charts according to the adjustment.

In some embodiments, the one or more charts may include a block diagram, a histogram, and/or a table.

In some embodiments, a method for tissue density analysis may include obtaining tissue density distribution data; displaying the obtained tissue density distribution data in one or more charts; adjusting the tissue density distribution data displayed in the one or more charts; and displaying the adjusted tissue density distribution data in the one or more charts.

According to another aspect of the present disclosure, a system is provided. The system may include at least one storage medium including a set of instructions, and at least one processor in communication with the at least one storage medium. When executing the set of instructions, the at least one processor may be configured to cause the system to obtain image data and tissue density distribution data; display the obtained tissue density distribution data on the image data in one or more color masks; adjust the tissue density distribution data displayed in the one or more color masks; and display adjusted tissue density distribution data in the one or more color masks.

In some embodiments, the tissue density distribution data may include a CT value based on the image data.

In some embodiments, the at least one processor may be configured to cause the system to adjust one or more tissue density segmentation thresholds.

In some embodiments, the at least one processor may be configured to cause the system to modify a tissue density segmentation threshold, add a tissue density segmentation threshold, and/or delete a tissue density segmentation threshold with annotation, mouse input, or voice input.

In some embodiments, the at least one processor may be configured to cause the system to update the tissue density distribution data in the one or more color masks simultaneously according to an adjustment result.

In some embodiments, the at least one processor may be configured to cause the system to update at least one of a color or statistics data of a same density segmentation in the one or more color masks simultaneously according to the adjustment result.

BRIEF DESCRIPTION OF THE DRAWINGS

In order to illustrate the technical solutions related to the embodiments of the present disclosure, brief introduction of the drawings referred to the description of the embodiments is provided below. Obviously, drawings described below are only some examples or embodiments of the present disclosure. Those having ordinary skills in the art, without further creative efforts, may apply the present disclosure to other similar scenarios according to these drawings. Unless stated otherwise or obvious from the context, the same reference numeral in the drawings refers to the same structure and operation.

DETAILED DESCRIPTION

As used in the disclosure and the appended claims, the singular forms "a," "an," and "the" include plural referents unless the content clearly dictates otherwise. The terms "including" and "comprising" are merely meant to include the steps and elements that are specifically identified, and such steps and elements do not constitute an exclusive list, and the method or device may also include other steps or elements. The term "based on" is "based at least in part on." The term "one embodiment" means "at least one embodiment"; the term "another embodiment" means "at least one additional embodiment." The relevant definitions of other terms will be given in the description below.

According to some embodiments of the present disclosure, flow charts are used to illustrate the operations performed by the system. It is to be expressly understood, the operations above or below may or may not be implemented in order. Conversely, the operations may be performed in inverted order, or simultaneously. Besides, one or more other operations may be added to the flow charts, or one or more operations may be omitted from the flow charts.

The present disclosure describes a method of tissue density analysis. A tissue density may be divided into one or more CT intervals based on CT values. Distributions of different CT intervals or density intervals in the tissue or lesion to be analyzed may be represented by a plurality of charts. By displaying the plurality of charts at the same time, the user may set the density interval of the tissue lesions easily, and obtain the density analysis results intuitively.

Figure 1:
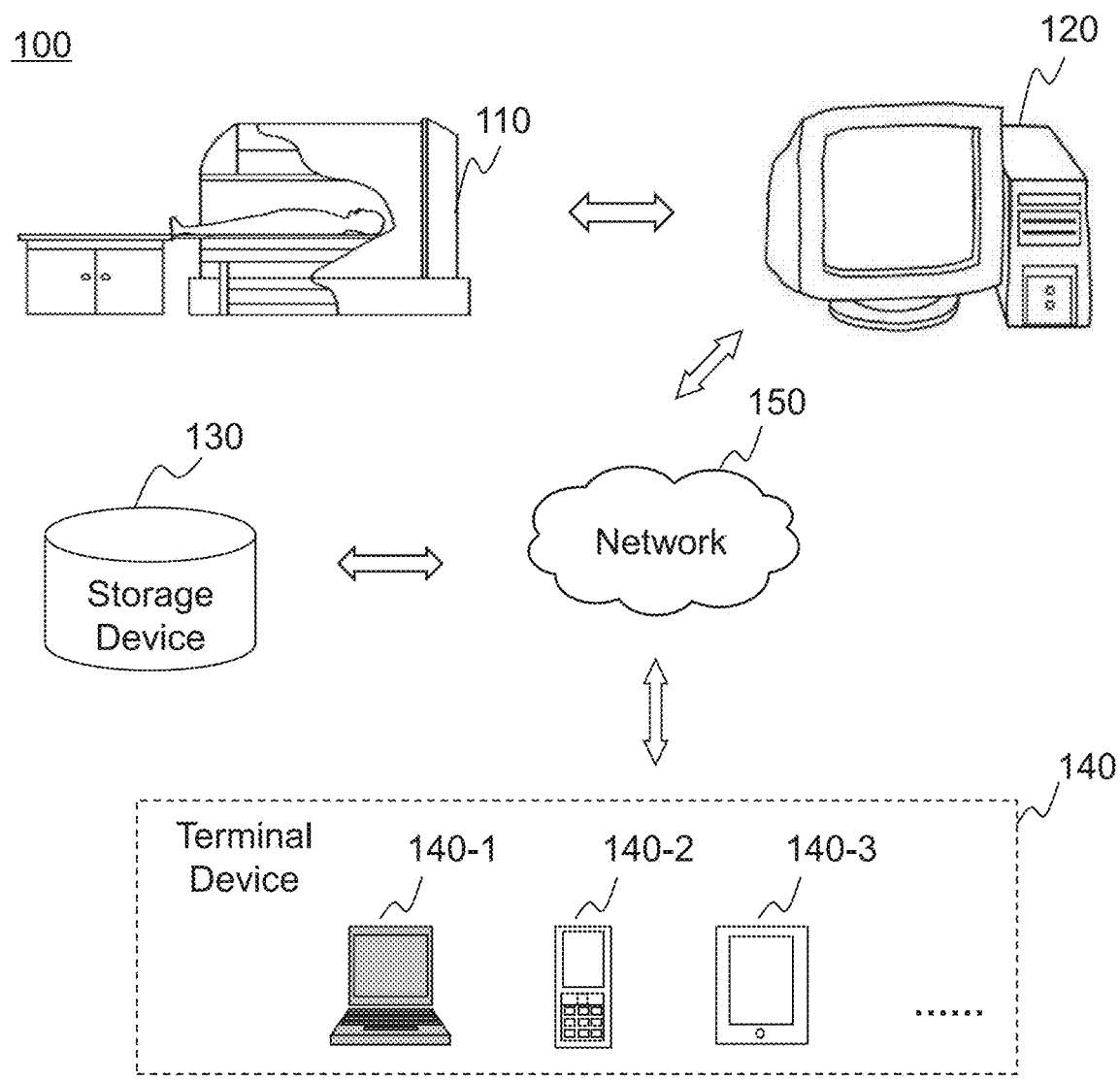
FIG. 1 is a schematic diagram of an application scenario illustrating a tissue density analysis system according to some embodiments of the present disclosure.

FIG. 1 is a schematic diagram of an application scenario illustrating an exemplary tissue density analysis system according to some embodiments of the present disclosure. As shown in FIG. 1, a tissue density analysis system 100 may include an imaging device 110, a storage device 130, and a tissue density analysis device 120.

The imaging device 110 may generate an image by scanning a target object. The image may be a medical image. For example, the image may be a head image, a chest image, an abdominal image, a pelvic image, a perineal image, a limb image, a spine image, a vertebra image, or the like. The head image may include a brain image, a skull image, or the like. The chest image may include an entire chest image, a heart image, a breast image, or the like. The abdominal image may include an entire abdominal image, a kidney image, a liver image, a lung image, or the like. The image may include, but not limited to, an omnidirectional digitized image, a digitized tomogram image, a phase contrast map, a computed radiography (CR) image, a multimodal image, or the like. The image may be a two-dimensional image or a three-dimensional image. The format of the image may include a JPEG format, a TIFF format, a GIF format, an FPX format, or the like. The image may be stored in the storage device 130, or be transmitted to the tissue density analysis device 120 for image processing.

The storage device 130 may store image and/or information related to the image. The image and the information related to the image may be provided by the imaging device 110, the tissue density analysis device 120, or an external device of the tissue density analysis system 100. For example, the storage device 130 may store user input information, information obtained from the network 150, or the like. The information related to the image may include an algorithm, a sample, a model, a parameter for image processing, real-time data during image processing, or the like. The storage device 130 may be a hierarchical database, a networked database, or a relational database. The storage device 130 may be a local database or a remote database. The storage device 130 or other storage devices in the tissue density analysis system 100 may digitize information and store the digitized information using a storage device that operates electrically, optically, or magnetically. In some embodiments, the storage device 130 or the other storage devices in the tissue density analysis system 100 may be a device that uses electrical energy to store information, such as a random-access memory (RAM), a read only memory (ROM), or the like. The random access memory may include, but is not limited to, a decimal counter, a select tube, a delay line memory, a Williams tube, a dynamic random access memory (DRAM), a static random access memory (SRAM), a thyristor random access memory (T-RAM), a zero capacitance random access memory (Z-RAM), or the like, or any combination thereof. The read-only memory may include, but is not limited to, a bubble memory, a magnetic button line memory, a thin film memory, a magnetic plate line memory, a magnetic core memory, a drum memory, an optical disk drive, a hard disk, a magnetic tape, a anon-volatile memory (NVRAM), a phase change memory, a magneto-resistive random storage memory, a ferroelectric random access memory, a non-volatile static random access memory, a programmable read-only memory, a shielded heap read memory, a floating connection gate random access memory, a nano random access memory, a track memory, a variable resistance memory, a programmable metallization unit, or the like, or any combination thereof. In some embodiments, the storage device 130 or the other storage devices in the tissue density analysis system 100 may be a device that uses magnetic energy to store information, such as a hard disk, a floppy disk, a magnetic tape, a magnetic core memory, a magnetic bubble memory, a USB flash drive, a memory, or the like. In some embodiments, the storage device 130 or the other storage devices in the tissue density analysis system 100 may be a device that optically stores information, such as a CD, a DVD, or the like. In some embodiments, the storage device 130 may be a device that stores information using a magneto-optical method, such as a magneto-optical disk, or the like. The access mode of the storage device 130 or other storage devices in the tissue density analysis system 100 may be a random storage, a serial access storage, a read-only storage, or the like, or any combination thereof. The storage device 130 or the other storage device in the tissue density analysis system 100 may be a non-permanent memory or a permanent memory. The storage device 130 described above is merely an example, and the storage device 130 used in the tissue density analysis system 100 may not be limited thereto.

The storage device 130 may be a part of the tissue density analysis device 120, a part of the imaging device 110, or may exist independently of the tissue density analysis device 120 and the imaging device 110. In some embodiments, the storage device 130 may be connected to other modules or devices in the tissue density analysis system 100 via the network 150. The connections between the storage device 130 and the other modules or devices in the tissue density analysis system 100 may include a wired connection, a wireless connection, or a combination thereof.

The tissue density analysis device 120 may obtain image data from the imaging device 110, and/or the storage device 130. The tissue density analysis device 120 may analyze the obtained image data. The analysis may include a tissue density analysis, an airway analysis, or the like. The tissue density analysis may include a tissue or lesion density display, a tissue or lesion density adjustment, or the like. The tissue density analysis device 120 may display tissue or lesion density analysis data to the user in a variety of forms simultaneously. The forms may include a table, a histogram, a CT value bar chart, or the like. The tissue density analysis device 120 may display the processed image data via a display device, store the processed data in the storage device 130, or transmit the processed data to a device other than the tissue density analysis system 100.

In some embodiments, the tissue density analysis device 120 may include one or more processors, storages, or the like. For example, the tissue density analysis device 120 may include a central processor (CPU), an application specific integrated circuit (ASIC), a dedicated instruction set processor (ASIP), an image processor (GPU), a physical computing processor (PPU), a digital signal processor (DSP), a field programmable gate array (FPGA), a programmable logic device (PLD), a controller, a micro control unit, a processor, a microprocessor, an advanced RISC machine processor, or the like, or any combination thereof.

In some embodiments, the tissue density analysis system 100 may also include one or more terminal devices 140. The terminal device 140 may perform information interaction with the imaging device 110, the storage device 130, and the tissue density analysis device 120. For example, the terminal device 140 may obtain processed image data from the tissue density analysis device 120. In some embodiments, the terminal device 140 may obtain image data from the imaging device 110 and transmit the image data to the tissue density analysis device 120 for image processing. The one or more terminal devices 140 may include a desktop 140-1, a handset 140-2, a tablet computer 140-3, or the like. The one or more terminal devices 140 may include one or more input devices, one or more control panels, or the like. For example, the one or more input devices may include a keyboard, a touch screen, a mouse, a voice input device, a scanning device, an information recognition device (such as a human eye recognition system, a fingerprint recognition system, a brain monitoring system, etc.), a remote controller, or the like.

The tissue density analysis system 100 may be connected to the network 150. The network 150 may be a wireless network, a mobile network, a wired network, or the like. The wireless network may include a Bluetooth, a WLAN, a Wi-Fi, a WiMax, or the like. The mobile network may include a 2G, a 3G, a 4G, or the like. The wired network may include a local area network (LAN), a wide area network (WANs), a private network, or the like.

The storage device 130 and the tissue density analysis device 120 in the tissue density analysis system 100 may execute operational instructions via a cloud computing platform. The cloud computing platform may include a storage cloud platform based on data storage, a computational cloud platform based on data processing, and an integrated cloud computing platform that combines computing, data storage and data processing. For example, image data generated by the tissue density analysis system 100 may be processed or stored by a cloud computing platform.

It should be noted that the above description of the tissue density analysis system 100 is merely provided for the purposes of illustration, and not intended to limit the scope of the present disclosure.

Figure 2:
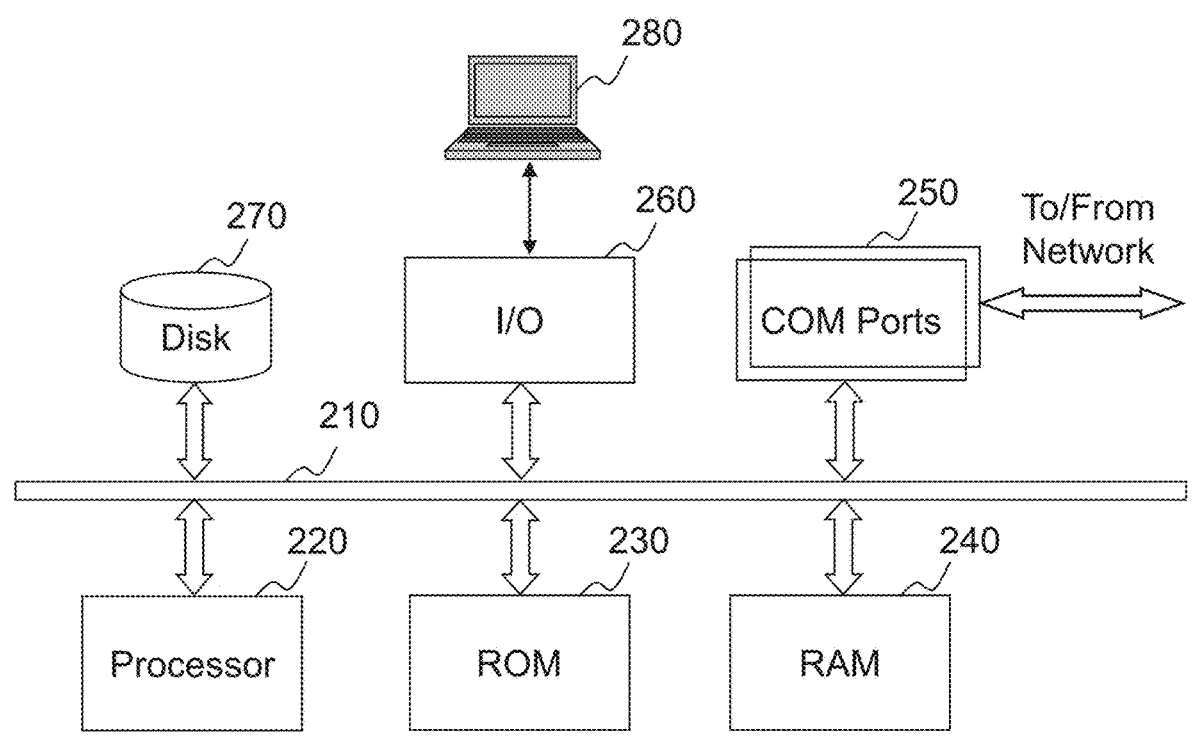
FIG. 2 is a schematic diagram of an exemplary system configuration illustrating a tissue density analysis device according to some embodiments of the present disclosure.

FIG. 2 is a schematic diagram of an exemplary system configuration illustrating a tissue density analysis device according to some embodiments of the present disclosure. As shown in FIG. 2, the tissue density analysis device 120 may include a data bus 210, a processor 220, a read only memory (ROM) 230, a random access memory (RAM) 240, a communication port 250, an input/output port 260, a hard disk 270, and a display 280 connected to the input/output port 260. The connection between hardware in the tissue density analysis device 120 may be wired, wireless, or a combination of thereof. The hardware may be local, remote, or a combination of thereof.

The data bus 210 may be configured to transfer data and/or information. In some embodiments, hardware in the tissue density analysis device 120 may transmit data via the data bus 210. For example, the processor 220 may send data to a storage or other hardware such as the input/output port 260 via the data bus 210. It should be noted that the data may be real data, an instruction code, state information, control information. In some embodiments, the data bus 210 may be an industry standard (ISA) bus, an extended industry standard (EISA) bus, a video electronic standard (VESA) bus, an external component interconnect standard (PCI) bus, or the like.

The processor 220 may be used for logic operations, data processing, and instruction generation. In some embodiments, the processor 220 may obtain data/instructions from an internal storage. The storage may include a read only memory (ROM), a random-access memory (RAM), a cache (not shown in FIG. 2), or the like. In some embodiments, the processor 220 may include a plurality of sub-processors configured to implement different functions of the system.

The read only memory 230 may be used for the power-on self-test of the tissue density analysis device 120, an initialization of each functional module in the tissue density analysis device 120, a driver of the input/output of the tissue density analysis device 120, or the like. In some embodiments, the read only memory may include a programmable read only memory (PROM), a programmable erasable read only memory (EPROM), or the like. The random-access memory 240 may be used to store an operating system, an application, data, or the like. In some embodiments, the random-access memory 240 may include a static random-access memory (SRAM), a dynamic random-access memory (DRAM), or the like.

The communication port 250 may be configured to connect the operating system with an external network to implement communications between them. In some embodiments, the communication port 250 may include an FTP port, an HTTP port, or a DNS port. The input/output port 260 may be configured to exchange and control data and information between an external device or a circuit and the processor 220. In some embodiments, the input/output port 260 may include a USB port, a PCI port, an IDE port, or the like.

The hard disk 270 may be configured to store information and data generated by the tissue density analysis device 120, or information and data received from outside the tissue density analysis device 120. In some embodiments, the hard disk 270 may include a mechanical hard disk (HDD), a solid-state hard disk (SSD), or a hybrid hard disk (HHD). The display 280 may be configured display information and data generated by the tissue density analysis system 100 to the user. In some embodiments, the display 280 may include a physical display, such as a display with a speaker, an LCD display, an LED display, an OLED display, an electronic ink display (E-Ink), or the like.

Figure 3:
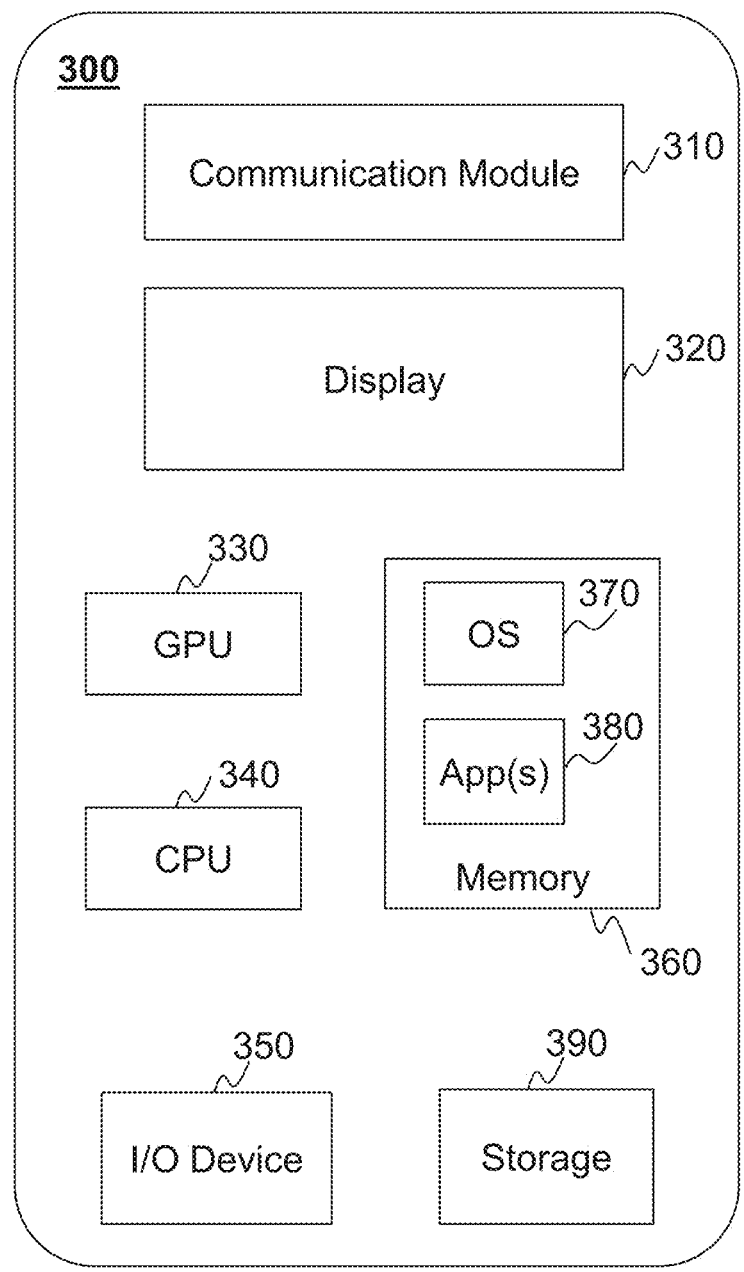
FIG. 3 is a schematic diagram illustrating an exemplary mobile device for implementing one or more specific systems in the present disclosure according to some embodiments of the present disclosure.

FIG. 3 is a schematic diagram illustrating an exemplary mobile device for implementing one or more specific systems in the present disclosure according to some embodiments of the present disclosure. As shown in FIG. 3, the mobile device 300 may include a terminal device 140. In some embodiments, the user may receive or transmit information related to the tissue density analysis system 100 via the mobile device 300. The mobile device 300 may include a smartphone, a personal digital assistant (PDA), a tablet computer, a handheld game player, smart glasses, a smart watch, a wearable device, a virtual reality device, a display enhancement device, or the like, or any combination thereof. In some embodiments, the mobile device 300 may include one or more central processors (CPUs) 340, one or more image processors (GPUs) 330, a display 320, a memory 360, one or more communication modules 310, a storage 390, and one or more input/output devices 350. The one or more communication modules 310 may be configured in the mobile device 300, or connected to the mobile device 300 as a removable external device. Further, the mobile device 300 may also include a system bus, a controller, or the like. As shown in FIG. 3, the central processor 340 may download the mobile device operating system (e.g., iOS, Android, Windows Phone, etc.) 370 and one or more applications 380 from the storage 390 into the memory 360. The one or more applications 380 may include a web page or other mobile application software (App) for receiving and transmitting information related to the tissue density analysis system 100. The user may obtain or provide information via the input/output device 350. The information may be transmitted to the tissue density analysis system 100, or a device unit in the tissue density analysis system 100.

In some embodiments, the computer hardware platform may be used as a hardware platform for one or more components (e.g., the tissue density analysis system 100 and a portion thereof), to implement their functions. The hardware components, the operating systems, and the programming languages may be inherently traditional, and those skilled in the art may apply these techniques to tissue density analysis. A computer with a user interface may be a personal computer (PC), other workstations or terminal devices. A programmed computer may serve as a server. Since those skilled in the art may be familiar with the structure, programming and general operations of the computer used in the present disclosure, detailed explanations may not be repeated herein.

Figure 4:
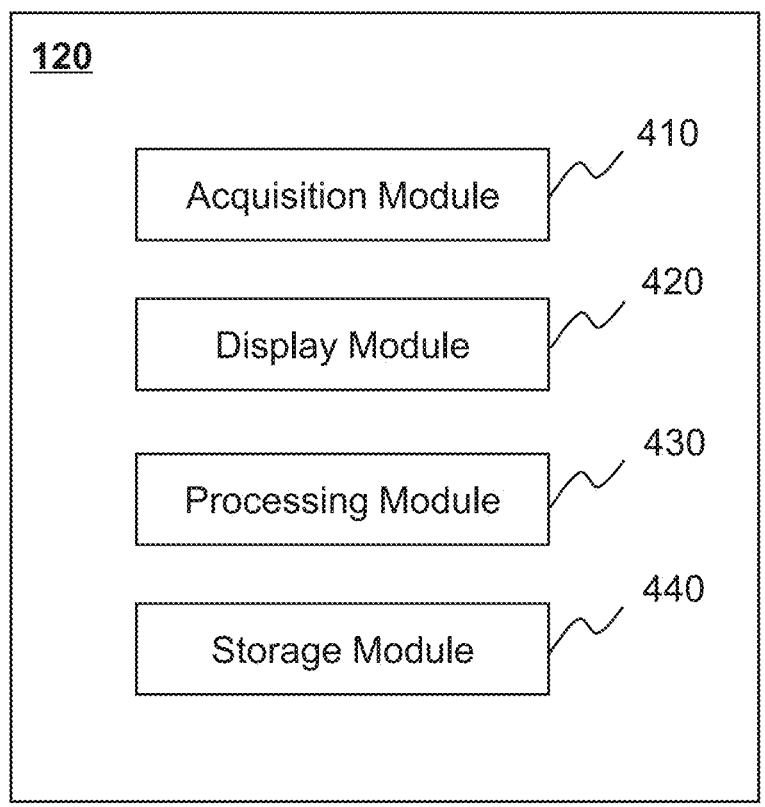
FIG. 4 is a schematic diagram illustrating an exemplary tissue density analysis device according to some embodiments of the present disclosure.

FIG. 4 is a schematic diagram illustrating an exemplary tissue density analysis device according to some embodiments of the present disclosure. In some embodiments, the tissue density analysis device 120 may include an acquisition module 410, a display module 420, a processing module 430, and a storage module 440. Connections between modules in the tissue density analysis device 120 may be wired, wireless, or a combination thereof. The module may be local, remote, or a combination thereof.

The acquisition module 410 may be configured to obtain image data. In some embodiments, the acquisition module 410 may obtain image data from the imaging device 110, the storage device 130, the storage module 440, or outside of the tissue density analysis system 100. The function of the acquisition module 410 may be implemented by the processor 220 in FIG. 2. For example, the acquisition module 410 may obtain original image data, digitized image data, an image model, an operational instruction, or the like, from the imaging device 110. As another example, the acquisition module 410 may obtain standard tissue density analysis image data, partial tissue density analysis image data, or the like, from the storage device 130 or the storage module 440. As another example, the acquisition module 410 may obtain standard tissue density analysis image data, image data that requires tissue density analysis, image data after tissue density analysis, or the like, from outside of the tissue density analysis system 100. In some embodiments, the image data may be a head image, a chest image, an abdominal image, a pelvic image, a perineal image, a limb image, a spine image, a vertebral image, or the like, including a lesion tissue. The image data may include, but is not limited to, an omnidirectional digitized image, a digitized tomogram, a phase contrast map, computed radiography (CR) image, a multimodal image, or the like. In the present disclosure, an image including a tissue or a lesion may be referred to as a medical image or an image. The image data may include pixel information, a CT value of each point in the image, a volume represented by each point in the image, an initial density interval and a volume distribution of the tissue to be analyzed, or the like. In some embodiments, the acquisition module 410 may send the obtained image data to the display module 420, the processing module 430, or the storage module 440. For example, the acquisition module 410 may send the obtained image data to the display module 420 for display. As another example, the acquisition module 410 may send the obtained image data to the processing module 430 for tissue density analysis or processing. As another example, the acquisition module 410 may send the obtained image data to the storage module 440 for storage. In some embodiments, the acquisition module 410 may receive a data acquisition instruction from the processor 220 and complete a corresponding data acquisition operation.

Figure 7A:
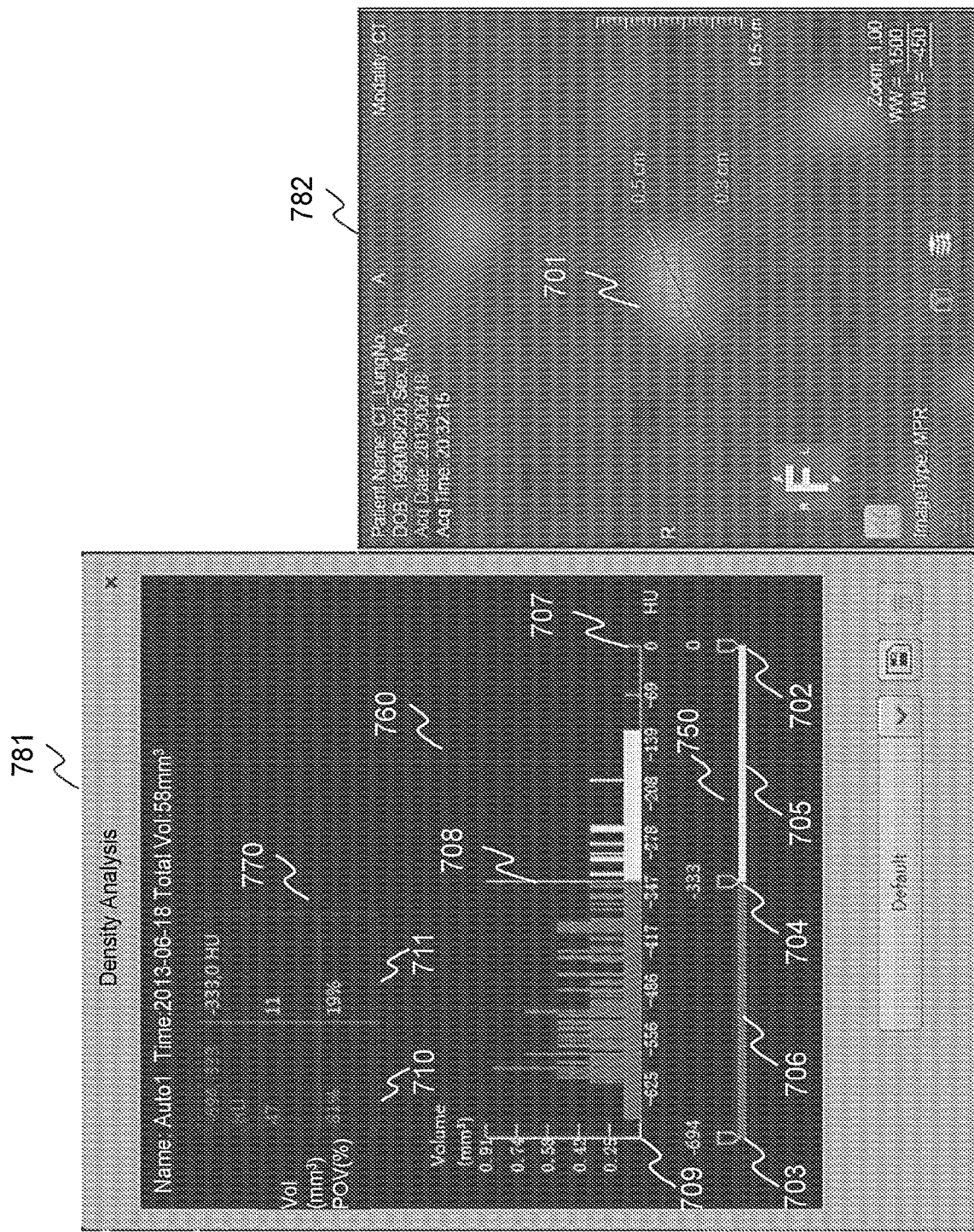
FIG. 7A is a schematic diagram illustrating an exemplary tissue density analysis preset by a system according to some embodiments of the present disclosure.

The display module 420 may be configured to display a target tissue or lesion in obtained image data. The function of the display module 420 may be implemented by the display 280 in FIG. 2. In some embodiments, the display module 420 may display the medical image of the target tissue and a corresponding CT value bar chart simultaneously. The CT value bar chart may represent a range of CT values. In some embodiments, the CT value bar chart may include one or more sliders. The one or more sliders may divide the CT values into one or more CT intervals or density segmentations. The one or more CT intervals may be represented by one or more color bars or grayscale bars. The color bar may be a line segment represented by one color, for example, red, orange, yellow, green, blue, purple, black, white, or the like. The grayscale bar may be a line segment represented by black, white, or a transition color from black to white. In some embodiments, the display module 420 may display a medical image of the target tissue, a CT value bar chart, a histogram, and/or a table corresponding to the target tissue, simultaneously. The histogram may be associated with the target tissue and the CT value bar chart. The histogram may represent a volume distribution of regions having different CT values in the target tissue. The table may be associated with the target tissue, the CT value bar and the histogram. The table may represent volumes and volume percentages of different CT intervals in the target tissue. In some embodiments, the medical image, the histogram, and the table of the target tissue may be divided into one or more regions according to one or more CT intervals of the CT value bar chart. For example, if the CT value bar chart has two CT intervals, the medical image of the target tissue may be divided into two regions, the histogram may be divided into two parts, and the table may be divided into two sets of data. In some embodiments, the display module 420 may represent a CT interval in one color. For example, a color of a region representing a CT interval in the medical image, the histogram, and the table of the target tissue may be consistent with a color representing the CT interval in the CT value bar chart. Specifically, the color of the data strip in a CT interval in the histogram may be consistent with the color of the color bar in the corresponding section in the CT value bar chart. A set of volume data, a set of volume percentage data, and the color of the corresponding CT value in the table may be consistent with the color of the color bar in the corresponding section in the CT value bar chart. In some embodiments, the display module 420 may represent a background of a displayed page in one or more colors. The colors may include, but is not limited to, red, orange, yellow, green, blue, purple, black, white, or the like. For example, the background color of the display page may be green. In some embodiments, the display module 420 may display, by one or more arrangements, the medical image of the target tissue and the CT value bar chart, the histogram, and/or the table representing a CT interval distribution on the medical image of the target tissue. The arrangement may include a left-right juxtaposition arrangement (as shown in FIG. 7A), an upper and lower juxtaposition arrangement, a wraparound arrangement centered on the medical image of the target tissue, or the like, or any combination thereof. In some embodiments, the display module 420 may display the image data in one or more languages. The one or more languages may include Chinese, English, Japanese, German, or the like. A specific embodiment may be described in FIG. 7A. The medical image of the target tissue, the CT value bar chart, the histogram and/or the table representing the CT interval distribution on the medical image of the target tissue may be displayed on a same display interface. In some embodiments, the medical image of the target tissue, the CT value bar chart, the histogram, and/or the table representing the CT interval distribution on the medical image of the target tissue may be displayed on different display interfaces. In some embodiments, the medical image of the target tissue, the CT value bar chart, the histogram, and/or the table representing the CT interval distribution on the medical image of the target tissue may be displayed on different display interfaces in different combinations. In some embodiments, the different display interfaces may include a tiled display or an overlapping display.

The processing module 430 may be configured to adjust a density segmentation or a CT interval. The processing module 430 may also be configured to determine a volume and a volume percentage of at least one CT interval. In some embodiments, the processing module 430 may adjust the division of the CT interval by adjusting one or more sliders in the CT value bar chart. For example, the processing module 430 may modify one or more CT intervals, add one or more CT intervals, or delete one or more CT intervals. In some embodiments, the processing module 430 may determine and adjust image data representing different CT intervals in the histogram and/or the table according to an adjustment result of the CT interval on the CT value bar chart. The image data in the CT value bar chart, the histogram, and/or the table may be adjusted or changed simultaneously, such that the data in each chart may correspond to each other. For example, if the CT intervals on the CT value bar chart changes from two intervals to three intervals, the processing module 430 may divide data in the histogram into three parts, and/or adjust data in the table to three groups. In some embodiments, the processing module 430 may determine a volume and a volume percentage corresponding to each section after the CT interval adjustment according to the image data obtained by the acquisition module 410 and the CT value bar chart. The image data may include a CT value of each point in the image, a volume represented by each point in the image, an initial density interval and a volume distribution of the tissue to be analyzed, or the like. In some embodiments, the processing module 430 may determine different colors for different CT intervals. The colors may include, but are not limited to, red, orange, yellow, green, blue, purple, black, white, or the like. For example, a CT value bar chart may have two CT intervals represented by yellow and purple color bars, respectively. When a new CT interval is added in the CT value bar chart, the processing module 430 may determine a color different from the colors of the other two CT intervals, e.g., green, for the added CT interval in the CT value bar chart, the histogram, and/or the table. As another example, a CT value bar chart may have four CT intervals represented by pink, blue, orange, and white color bars, respectively. The processing module 430 may determine other colors for the four CT intervals in the histogram, and/or the table corresponding to the CT value bar chart, e.g., red, gold, purple, and yellow, respectively. In some embodiments, the processing module 430 may adjust the background color of the displayed page. In some embodiments, the processing module 430 may adjust the arrangement of the CT image of the target tissue, the CT value bar chart, the histogram, and/or the table representing the CT interval distribution on the medical image of the target tissue. The arrangement may include a left-right juxtaposition arrangement, an upper and lower juxtaposition arrangement, a wraparound arrangement centered on the medical image of the target tissue, or the like, or any combination thereof. For example, the processing module 430 may adjust the arrangement of the medical image, the CT value bar chart, the histogram, and/or the table from the left-right juxtaposition arrangement to the upper and lower juxtaposition arrangement. The arrangement may refer to an arrangement in any order. For example, the CT value bar chart, the medical image, the histogram, and/or the table may be arranged from left to right successively. As another example, the table, the histogram, the CT value bar chart, and the medical image may be arranged from upper to lower successively. The processing module 430 may send the processed image data to the display module 420 for display, or to the storage module 440 for storage.

The storage module 440 may be configured to store image data or operational instructions. The function of the storage module 440 may be implemented by the hard disk 270, the read only memory 230, the random-access memory 240 shown in FIG. 2, or the like, or any combination thereof. The storage module 440 may store image data and/or operation instructions obtained by the acquisition module 410, real time data generated by the processing module 430, processed image data, or the like. The operational instructions may include a volume and/or volume percentage algorithm, a permutation algorithm, a color configuration algorithm, or the like. The storage module 440 may include, but not limited to, various types of storage devices such as a solid-state hard disk, a mechanical hard disk, a USB flash memory, an SD memory card, an optical disk, a random-access memory (RAM), or a read only memory (ROM). The storage module 440 may be a storage device included in the system, or an external storage device of the system, such as a storage on a cloud storage server.

It should be noted that the above description of the tissue density analysis device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The modules may be combined in any way. The modules may form a subsystem and be connected to other modules. For example, the acquisition module 410 and the display module 420 may be integrated into a single module.

Figure 5:
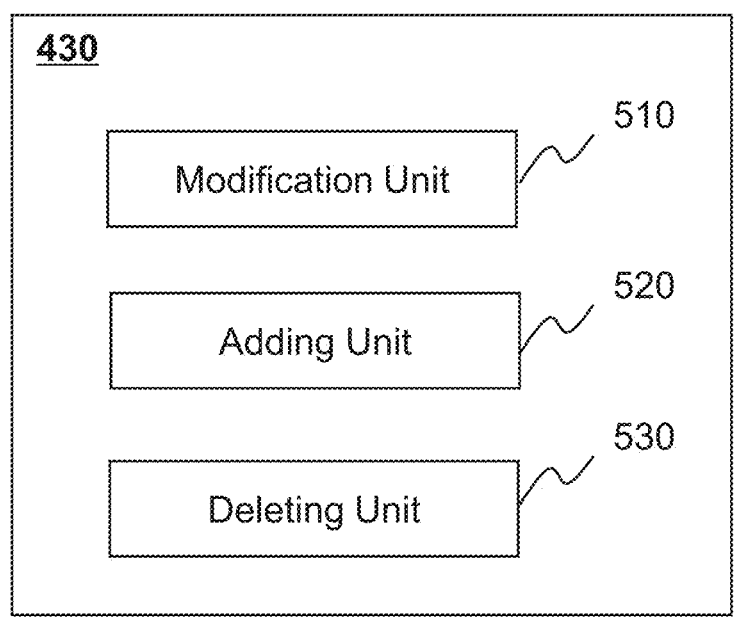
FIG. 5 is a schematic diagram illustrating an exemplary processing module according to some embodiments of the present disclosure.

FIG. 5 is a schematic diagram illustrating an exemplary processing module according to some embodiments of the present disclosure. In some embodiments, the processing module 430 may include a modification unit 510, an adding unit 520, and a deleting unit 530. The connections between modules in the processing module 430 may be wired, wireless, or a combination thereof. The module may be local, remote, or a combination thereof.

Figure 8:
FIG. 8 is a schematic diagram illustrating an exemplary numerical display manner on a CT value bar chart according to some embodiments of the present disclosure.

The modification unit 510 may be configured to modify a density segmentation or a CT interval. In some embodiments, the modification unit 510 may modify the CT interval by moving a slider on the CT value bar chart. For example, the modification unit 510 may move the slider left and right via a mouse, a screen touch, a voice, or the like. In some embodiments, the modification unit 510 may modify the CT interval by modifying the CT value corresponding to the slider on the CT value bar chart. The CT value corresponding to the slider may be displayed above the CT value bar chart or the slider. The CT value corresponding to the slider may be displayed below the CT value bar chart or the slider. As shown in FIG. 8, the CT value above the CT value bar chart or the slider is reasonably arranged to avoid a layout problem includes threshold information overlaps or a densely arrangement due to a small segmentation or CT interval. For example, the modification unit 510 may modify the CT interval to a new CT interval by clicking or double-clicking the CT value corresponding to a slider on the CT value bar chart and inputting the new CT value. In some embodiments, the modification unit 510 may adjust the CT interval on the CT value bar chart by modifying the CT value or the CT interval in the table. In some embodiments, the modification unit 510 may determine and adjust image data representing different CT intervals in the histogram and/or the table according to the modified CT interval. The image data may include volumes and/or volume percentages, or the like, of different CT intervals in the tissue to be analyzed. In some embodiments, the modification unit 510 may adjust colors of different CT intervals. For example, a CT value bar chart may have three CT intervals represented by blue, green, and orange color bars, respectively. The modification unit 510 may adjust the colors of the corresponding three CT intervals in the CT value bar chart, the histogram, and/or the table to white, purple, and gold, respectively. In some embodiments, the modification unit 510 may adjust an arrangement of the medical image of the target tissue, the CT value bar chart, the histogram, and/or the table. For example, the modification unit 510 may arrange the CT value bar chart, the histogram, and/or the table in an upper and lower juxtaposition arrangement. The modification unit 510 may arrange the medical image of the target tissue, and the CT value bar chart, the histogram, and/or the table in a left-right juxtaposition arrangement. The modification unit 510 may adjust this arrangement to a wraparound arrangement centered on the medical image of the target tissue. The CT value bar chart, the histogram, and the table may be arranged on an upper side, a left side, and a right side of the medical image of the target tissue.

The adding unit 520 may be configured to add a density segmentation or a CT interval. In some embodiments, the adding unit 520 may add a CT interval on the CT value bar chart. For example, the adding unit 520 may add a CT interval by clicking or double clicking a point on the CT value bar chart. The adding unit 520 may determine a CT value of the CT interval by sliding the slider left and right. As another example, the adding unit 520 may click or double click a point on the CT value bar chart, and modify a CT value corresponding to the point, to add a new CT interval. As another example, the adding unit 520 may add a CT interval by voice. In some embodiments, the adding unit 520 may determine and adjust image data representing different CT intervals in the histogram and/or the table based on the adjusted CT intervals. The image data may include volumes and/or volume percentages of different CT intervals in the tissue to be analyzed, or the like. In some embodiments, the adding unit 520 may determine a color for a newly added CT interval. For example, a CT value bar chart may have two CT intervals represented by orange and blue color bars, respectively. When a new CT interval is added in the CT value bar chart, the adding unit 520 may determine a color for the newly added CT interval on the CT value bar chart, the histogram, and/or the table. The color may be different from the colors of the two CT intervals, such as white.

The deleting unit 530 may delete a density segmentation or a CT interval. In some embodiments, the deleting unit 530 may delete one or more CT intervals from the CT value bar chart. For example, the deleting unit 530 may delete a CT segment value corresponding to a slider by moving a slider up and down. Therefore, two CT intervals including the CT segment value may be adjusted to one CT interval. The up and down movement may be implemented by a mouse, a screen touch, or the like. The CT segment value may be any CT value between two endpoints of the CT value bar chart. As another example, the deleting unit 530 may delete one or more CT intervals by modifying a CT segment value to be deleted to a CT segment value to be reserved. As another example, the deleting unit 530 may delete a CT interval by voice. In some embodiments, the deleting unit 530 may determine and adjust image data representing different CT intervals in the histogram and/or the table based on the adjusted CT interval. The image data may include volumes and/or volume percentages of different CT intervals in the tissue to be analyzed, or the like. In some embodiments, the deleting unit 530 may modify colors of two intervals including the deleted CT segment value to a same color. The color may be any one of the colors of the original two intervals, or may be a third color different from the colors of the original two intervals. For example, a CT value bar chart may have three CT intervals represented by red, green, and blue color bars, respectively. When a CT segment value is deleted from the CT value bar chart, and the CT segment value is located between the two CT intervals represented by the green and blue color bars respectively, the deleting unit 530 may change the CT intervals represented by the green and blue color bars to a blue color bar. As another example, the deleting unit 530 may change the two CT intervals represented by the green and blue color bars to a new color bar, such as a yellow color bar.

It should be noted that the above description of the processing module 430 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. The modules may be combined in any way. The modules may form a subsystem and be connected to other modules. For example, the modification unit 510 may further be divided into a CT interval modification unit, a color modification unit, an arrangement modification unit, or the like. As another example, the modification unit 510 may be integrated with the adding unit 520 or the deleting unit 530.

Figure 6:
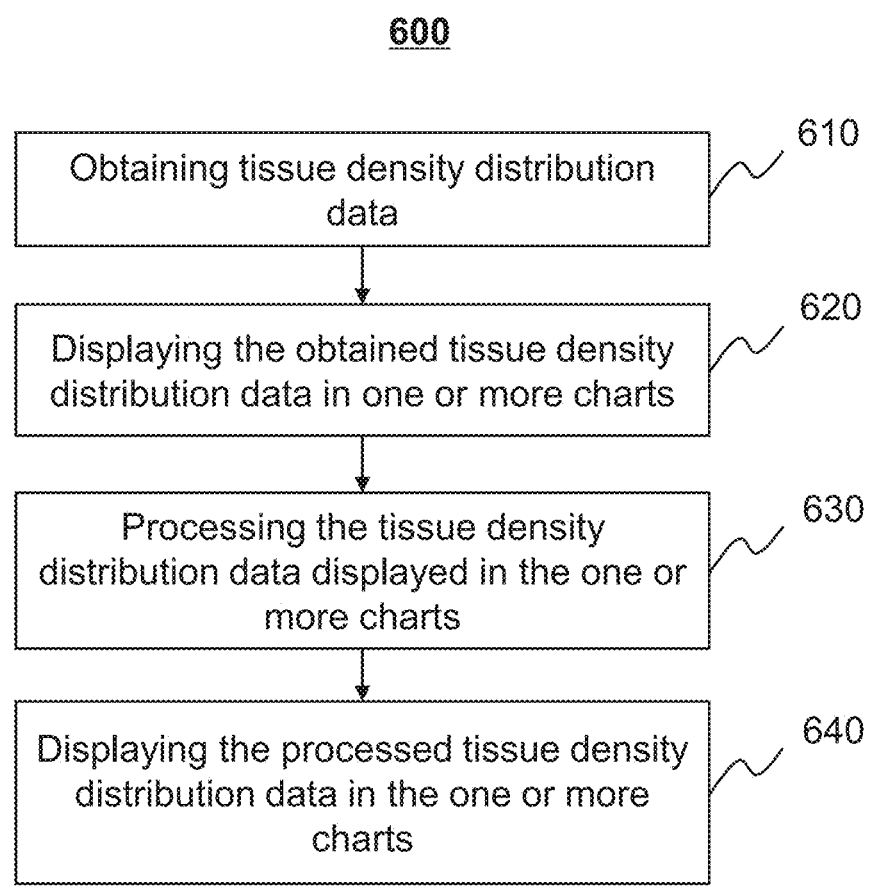
FIG. 6 is a flowchart illustrating an exemplary process for analyzing tissue density according to some embodiments of the present disclosure.

FIG. 6 is a flowchart illustrating an exemplary process 600 for analyzing tissue density according to some embodiments of the present disclosure. In 610, the tissue density analysis device 120 may obtain tissue density distribution data. The tissue density distribution data may include an image including a tissue to be density-analyzed, a CT value of each point in the image, a volume represented by the each point in the image, an initial density interval and a volume distribution of the tissue to be density-analyzed, or the like. In some embodiments, the tissue density distribution data may be obtained by the acquisition module 410. For example, the tissue density distribution data may be obtained by the acquisition module 410 via a network transmission, a hardware storage device transmission, or the like.

In 620, the tissue density analysis device 120 may display the obtained tissue density distribution data in one or more charts. The charts may include a medical image, a CT value bar chart, a histogram, a table, or the like. In some embodiments, the obtained tissue density distribution data may be displayed by the medical image and the CT value bar chart. Specifically, an image of the tissue or lesion to be analyzed may be displayed by the medical image. The medical image may be zoomed in or zoomed out. The CT interval of the tissue or lesion to be analyzed may be displayed by the CT value bar chart. In some embodiments, the obtained tissue density distribution data may be displayed by the medical image, the CT value bar chart, the histogram, and/or the table. Specifically, a lesion volume corresponding to different CT values of the tissue or lesion to be analyzed may be displayed by the histogram. The lesion volume and volume percentage corresponding to different CT values or CT intervals of the tissue or lesion to be analyzed may be displayed in the table. The volume percentage may be determined based on a total volume of the tissue or lesion to be analyzed. In some embodiments, the tissue density analysis device 120 may display one or more charts including the tissue density distribution data in one or more arrangements. For example, the one or more charts may be arranged in a left-right juxtaposition arrangement, an upper and lower juxtaposition arrangement, a wraparound arrangement, or the like, or any combination thereof. As shown in FIG. 7A, the CT value bar chart, the histogram, and the table may be arranged in an upper and lower juxtaposition arrangement. The CT value bar chart, the histogram, the table, and the medical image may be displayed in a left-right juxtaposition arrangement. In some embodiments, the tissue density analysis device 120 may display the background in one or more colors. The display colors of the background may include, but not limited to, black, green, pink, white, or the like. In some embodiments, the tissue density analysis device 120 may display colors of different CT intervals in the chart based on the color of the background. The display colors of a same CT interval in different charts may be the same. The display color of the CT interval in the chart may be different from the display color of the background. For example, if the display color of the background is green, and the CT values has three intervals, the colors of the three CT intervals in the medical image, the CT value bar chart, the histogram, and/or the table may be yellow, red, and purple, respectively.

In 630, the tissue density analysis device 120 may process the tissue density distribution data displayed in the one or more charts. In some embodiments, the tissue density analysis device 120 may adjust the tissue density distribution data by adjusting a density segmentation or a CT interval in the one or more charts. For example, the tissue density analysis device 120 may modify one or more CT intervals, add one or more CT intervals, or delete one or more CT intervals. In some embodiments, the CT interval may be adjusted by moving a slider on the CT value bar chart left and right. For example, a slider may be located on the CT value bar chart at a position where the CT value is −100, and the slider may be moved to a new CT segment value position, for example, −300, via a mouse or a screen touch. In some embodiments, the CT interval may be adjusted by moving the slider on the CT value bar chart by voice. In some embodiments, a CT interval may be added at any point on the CT value bar chart with mouse input (e.g., click, double click), or voice input. For example, if a CT segment value to be added is −400, a position between two endpoints of the CT value bar chart other than the CT segment value may be clicked or double-clicked, to obtain a slider corresponding to the position. The CT value corresponding to the slider may be modified to the CT segment value of −400, and a new CT interval may be added. Accordingly, a CT interval or a segmentation region may be added in the medical image, the histogram, and/or the table. In some embodiments, a CT segment value may be deleted by moving the slider on the CT value bar chart up and down, thereby deleting a CT interval. For example, the CT value bar char may include four CT segment values. The four CT segment values may include two endpoints of the CT value bar chart, a position corresponding to a CT value of −100, and a position corresponding to a CT value of −500. A CT segment value to be deleted is −100. A slider corresponding to the CT value of −100 may be moved to the top or bottom of the CT value bar chart via a mouse or a screen touch, and the CT segment value of −100 may be deleted. The CT intervals on the left and right sides of the segmentation value may be combined into one CT interval. In some embodiments, the CT segment value to be deleted may be modified to a CT segment value to be reserved, thereby deleting one or more CT intervals. For example, the CT segment value −100 may be deleted by modifying the CT segment value from −100 to −500, or a CT value corresponding to an endpoint of the CT value bar chart.

In some embodiments, the tissue density analysis device 120 may determine and adjust image data representing different CT intervals in the histogram and/or the table according to the adjusted CT intervals. For example, a corresponding volume and volume percentage in the histogram and/or the table may be redetermined based on the adjusted CT intervals. The volume or the volume percentage may be determined based on a CT value of each point in the image obtained by the acquisition module 410, a volume represented by the each point of the image, an initial density interval, a volume distribution of the tissue to be analyzed, or the like. In some embodiments, the tissue density analysis device 120 may adjust the displayed color of the background and/or the colors of different CT intervals in the chart. For example, the display color of the background may be green. The CT values may have three intervals. The colors of the medical image, the CT value bar chart, the histogram, and/or the table may be yellow, green, and purple, respectively. The colors of the three CT intervals may be adjusted to orange, red, and white, respectively. As another example, the CT interval represented by green may be adjusted to a new color, such as gray. In some embodiments, the tissue density analysis device 120 may adjust the arrangement of the medical image, the CT value bar chart, the histogram, and/or the table of the target tissue. The arrangement may include a left-right juxtaposition method, an upper and lower juxtaposition method, a wraparound arrangement centered on a medical image of the target tissue, or the like. In some embodiments, the tissue density analysis device 120 may perform a density analysis on lung tissue, and perform an airway analysis according to divided CT intervals of the lung tissue.

In 640, the tissue density analysis device 120 may display the processed tissue density distribution data in one or more charts. The processed tissue density distribution data may include tissue density distribution data after density segmentation, CT interval modification, CT interval addition, and/or CT interval deletion, the medical image, a color of the CT value bar chart, the histogram, and/or the table, the tissue density distribution data after arrangement adjustment, the tissue density distribution data after changing the color of the background. Accordingly, the medical image, the CT value bar chart, the histogram and/or the table of the tissue or lesion to be density-analyzed may be combined, displayed, and processed. The user may set the density segmentation of the tissue or lesion based on CT values easily, or observe a result of density analysis intuitively.

It should be noted that the above description of the analysis of the tissue density is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 620 and operation 630 may be performed simultaneously.

In some embodiments, the tissue density analysis device 120 may display the tissue density distribution data on the image data in one or more color masks. For example, the tissue density analysis device 120 may display one or more points in different CT intervals on the image data (e.g., a medical image) in different color masks (e.g., a red mask, a yellow mask, a blue mask). The tissue density analysis device 120 may adjust the tissue density distribution data displayed in the one or more color masks. The tissue density analysis device 120 may display adjusted tissue density distribution data in the one or more color masks.

FIG. 7A is a schematic diagram illustrating an exemplary tissue density analysis preset by a system according to some embodiments of the present disclosure. As shown in FIG. 7A, 782 refers to an image including a tissue or lesion, 701 refers to the tissue or lesion in the image 782 for tissue density analysis. As shown in FIG. 7A, 781 refers to a preset tissue density distribution map corresponding to the tissue density analysis region 701. The preset tissue density distribution map 781 may include a CT value bar chart 750, a histogram 760, and a table 770. The CT value bar chart 750 may represent CT values of the tissue density analysis region 701. For example, 702 may represent a CT value of 0, and 703 may represent a CT value of −694. The position of each slider between 702 and 703 may represent a density segmentation threshold. For example, 704 may represent a density segmentation threshold of −333. 705 and 706 may represent a region in which the density value is a CT value between 0 and −333, and a region in which the density value is a CT value between −333 to −694, respectively. 705 and 706 may be displayed in different colors. For example, 705 may be displayed in green, and 706 may be displayed in orange. The histogram 760 may represent volumes of different density segmentations in the tissue density analysis region 701. For example, 707 may correspond to 702 in the CT value bar chart 750. An ordinate value of 707 may be 0, which may indicate that the tissue density analysis region 701 does not include a region with a CT value of 0. 709 may correspond to 703 in the CT value bar chart 750. An ordinate value of 709 is 0, which may indicate that the tissue density analysis region 701 does not include a region with a CT value of −694. 708 may correspond to 704 in the CT value bar chart 750. An ordinate value of 708 may be about 0.91, which may indicate that a volume in the tissue density analysis region 701 with the CT value of −333 is about 0.91 mm$^3$. The table 770 may represent volumes and volume percentages of different density segmentations in the density analysis region. For example, 710 may represent that a volume of a region with CT values between −694 and −333 is 47 mm$^3$, and a volume percentage in the tissue density analysis region 701 is 81%. 710 may correspond to 706 in the CT value bar chart 750, and a region between 709 and 708 in the histogram 760. 711 may represent that a volume of a region with CT values between −333 and 0 is 11 mm$^3$, and a volume percentage in the tissue density analysis region 701 is 19%. 711 may correspond to 705 in the CT value bar chart 750, and a region between 708 and 707 in the histogram 760. The region density analysis region 701 shown in FIG. 7A may have two regions with significantly different colors, corresponding to the two density segmentations in the preset density distribution map 781 in FIG. 7B.

Figure 7B:
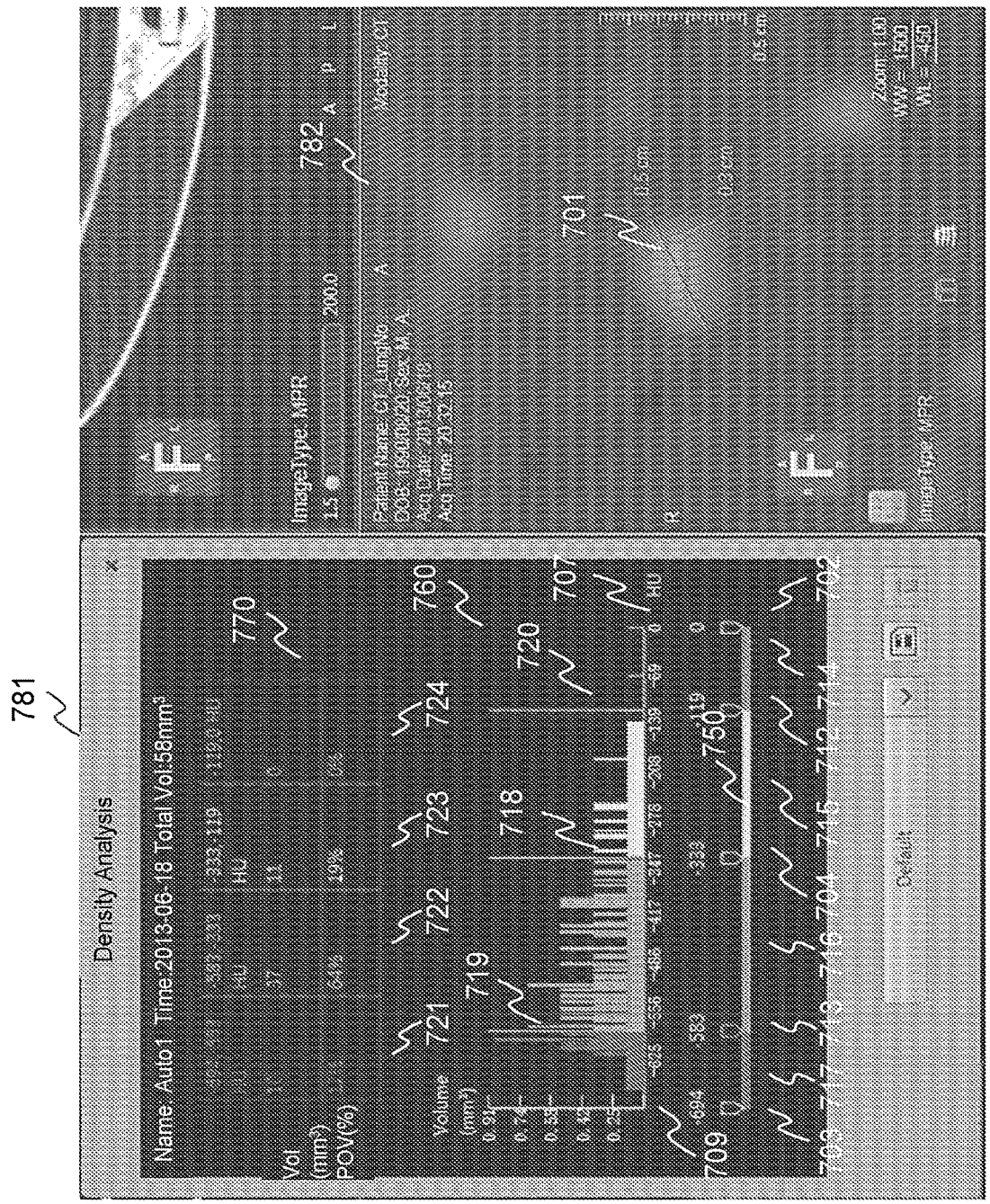
FIG. 7B is a schematic diagram illustrating an exemplary tissue density analysis that adds a density segmentation according to some embodiments of the present disclosure.

FIG. 7B is a schematic diagram illustrating an exemplary tissue density analysis that adds a density segmentation according to some embodiments of the present disclosure. As shown in FIG. 7B, 782 refers to an image including a tissue or lesion, and 701 refers to the tissue or lesion to be analyzed in the image 782. As shown in FIG. 7B, 781 refers to a tissue density distribution map after adding a density segmentation or a CT interval corresponding to the tissue density analysis region 701. As shown, the CT value bar chart 750 may include four density segmentations, such as, 714, 715, 716, and 717, respectively. Accordingly, the histogram 760 may also be divided into four sections. The density segmentation point positions may include 707, 720, 718, 719, and 709, respectively. The table 770 may also be divided into four parts. 721 may represent that a volume of a region with CT values between −694 and −583 is 10 mm$^3$, and a volume percentage in the tissue density analysis region 701 is 17%. 721 may correspond to 717 in the CT value bar chart 750, and a region between 709 and 719 in the histogram 760. 722 may represent that a volume of a region with CT values between −583 and −333 is 37 mm$^3$, and a volume percentage in the tissue density analysis region 701 is 64%. 722 may correspond to 716 in the CT value bar chart 750 and a region between 719 and 718 in the histogram 760. 723 may represent that a volume of a region with CT values between −333 and −119 is 11 mm$^3$, and a volume percentage in the tissue density analysis region 701 is 19%. 723 may correspond to 715 in the CT value bar chart 750, and a region between 718 and 720 in the histogram 760. 724 may represent that the tissue density analysis region 701 does not include a region with CT values between −119 and 0. 724 may correspond to 714 in the CT value bar chart 750, and a region between 720 and 707 in the histogram 760. In some embodiments, the density segmentation may be added by clicking a specified point on the CT value bar chart 750 via a mouse. For example, a density segmentation point 713 may be added by clicking a position indicating that the CT value is −583 on the CT value bar chart 750. As another example, a density segmentation point 712 may be added by clicking a position indicating that the CT value is −119 on the CT value bar chart 750. In some embodiments, a density segmentation may be added by clicking any point on the CT value bar chart 750 via a mouse, and modifying the CT value above the point into a CT value of a specified point. For example, a slider with a CT value of −360 on the CT value bar chart 750 may be obtained by clicking a point with a CT value of −360. A density segmentation may be added at a position with a CT value of −583 by modifying the value above the slider from −360 to −583 via clicking. As another example, a slider with a CT value of −600 on the CT value bar chart 750 may be obtained by clicking a point with a CT value of −600. A density segmentation may be added at a position with a CT value of −119 by modifying the value above the slider from −600 to −119 via clicking. In some embodiments, by adding the density segmentation on the CT value bar chart 750, the segment regions in the histogram 760 and the table 770 may also be changed accordingly. At the same time, a number (or count) of regions in the tissue density analysis region 701 may also be increased. For example, according to the density segmentations of the CT value bar chart 750 in FIG. 7B, the tissue density analysis region 701 may be divided into four regions. In some embodiments, colors of different density segmentation regions in the tissue density analysis region 701 may be the same as colors of different density segmentation regions in the CT value bar chart 750, the histogram 760, and the table 770, and may change simultaneously.

Figure 7C:
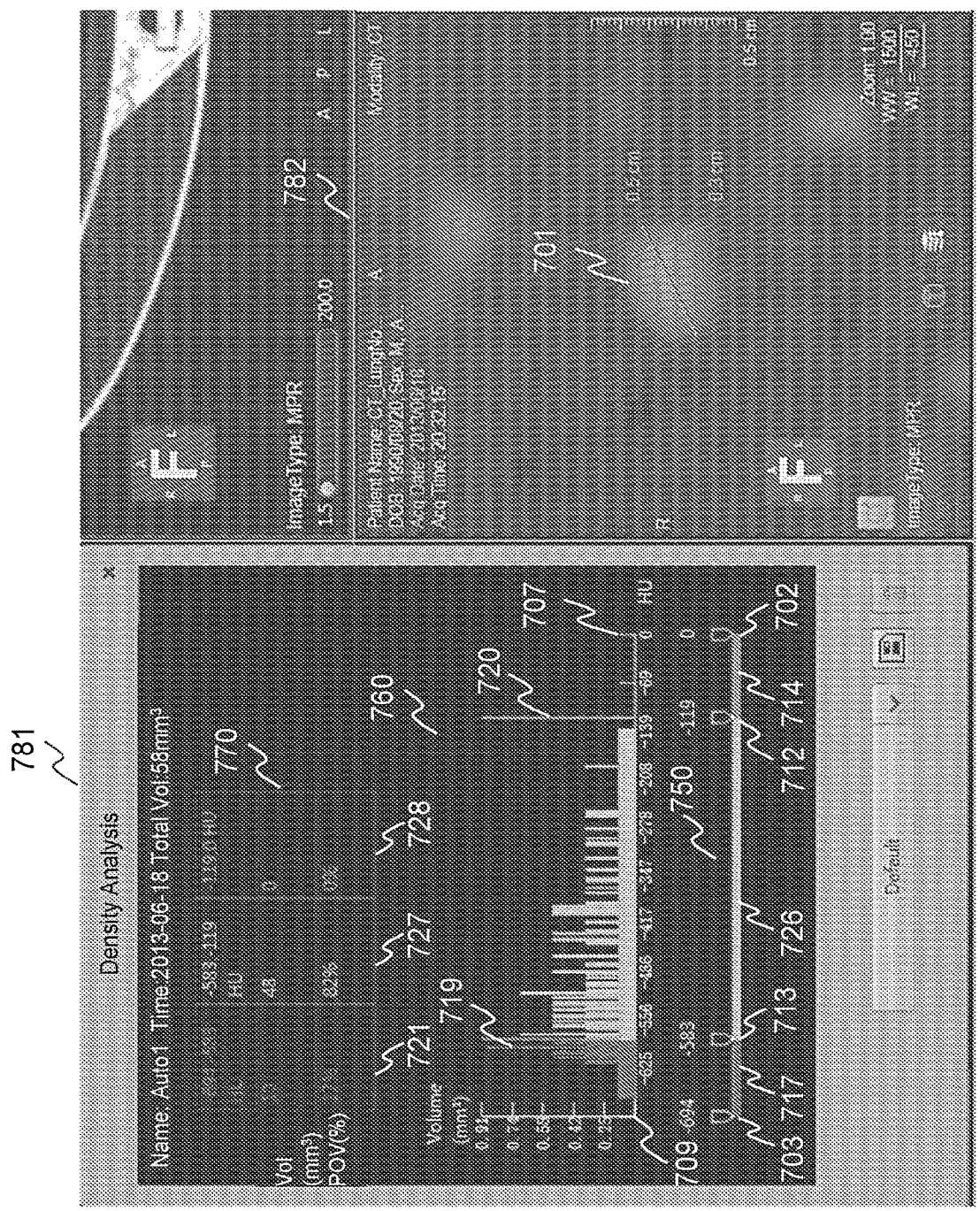
FIG. 7C is a schematic diagram illustrating an exemplary tissue density analysis that deletes a density segmentation according to some embodiments of the present disclosure.

FIG. 7C is a schematic diagram illustrating an exemplary tissue density analysis that deletes a density segmentation according to some embodiments of the present disclosure. As shown in FIG. 7C, 782 refers to an image including a tissue or lesion, and 701 refers to the tissue or lesion in the image 782 to be density-analyzed. As shown in FIG. 7C, 781 refers to a tissue density distribution map corresponding to the tissue density analysis region 701 after one or more density segmentations or CT intervals are deleted in the density segmentation in FIG. 7B. As shown, the CT value bar chart 750 may include three density segmentations, such as 714, 726, and 717, respectively. Accordingly, the histogram 760 may also be divided into three parts, with 707, 720, 719, and 709 as density segmentation point positions, respectively. The table 770 may also be divided into three parts. 721 may represent that a volume of a region with CT values between −694 and −583 is 10 mm$^3$, and a volume percentage in the tissue density analysis region 701 is 17%. 721 may correspond to 717 in the CT value bar chart 750 and a region between 709 and 719 in the histogram 760. 727 may represent that a volume of a region with CT values between −583 and −119 is 48 mm$^3$, and a volume percentage in the tissue density analysis region 701 is 82%. 727 may correspond to 726 in the CT value bar chart 750, and a region between 713 and 712 in the histogram 760. 728 may represent that the tissue density analysis region 701 does not include a region with CT values between −119 and 0. 728 may correspond to 714 in the CT value bar chart 750 and a region between 720 and 707 in the histogram 760. In some embodiments, a density segmentation may be deleted by moving the slider up and down. For example, if a slider with the CT value of −333 is the density segmentation value to be deleted, the density segmentations 716 and 715 in FIG. 7B may be deleted by moving a slider with the CT value of −333 on the CT value bar chart 750 up and down. In some embodiments, a density segmentation may be deleted by modifying a value of the slider to be deleted to a CT value of the density segmentation point to be reserved, or a CT value of a specific density segmentation point. For example, the density segmentation value with a CT value of −333 may be deleted by modifying a value above the slider with a CT value of −333 on the CT value bar chart 750 to 0, −119, −583, or −694. A density distribution map may be determined, as shown in FIG. 7C. In some embodiments, by deleting the density segmentation on the CT value bar chart 750, the segment regions in the histogram 760 and the table 770 are also be changed accordingly. At the same time, partitions in the tissue density analysis region 701 may also be reduced. For example, according to the density segmentation in the CT value bar chart 750 in FIG. 7C, the tissue density analysis region 701 may be divided into three regions.

Having thus described the basic concepts, it may be rather apparent to those skilled in the art after reading this detailed disclosure that the foregoing detailed disclosure is intended to be presented by way of example only and is not limiting. Various alterations, improvements and modifications to the present disclosure may occur and are intended to those skilled in the art, though not explicitly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, certain features, structures, or characteristics may be combined as suitable in one or more embodiments of the present disclosure.

Moreover, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, various aspects of the present disclosure may be implemented entirely hardware, entirely software (including firmware, resident software, micro-code, etc.), or combining hardware and software. The above hardware or software may be referred to as "data block", "module", "engine", "unit", "component" or "system". Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicated, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python, or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for Example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." Unless otherwise stated, "about," "approximate," or "substantially" may indicate ±20% variation of the value it describes. Accordingly, in some embodiments, the numerical parameters set forth in the written description and attached claims are approximations that may vary depending upon the desired properties sought to be obtained by a particular embodiment. In some embodiments, the numerical parameters may take a prescribed effective digit into account and adopt a general method to approximate the numerical parameters. Notwithstanding that the numerical ranges and parameters setting forth the broad scope of some embodiments of the application are approximations, the numerical values set forth in the specific examples are reported as precisely as practicable.

For each of the patents, patent applications, patent application publications and other materials, such as articles, books, instructions, publications, documents, articles, etc., cited in this application are hereby incorporated by reference in their entirety. Application history documents that are inconsistent or conflicting with the contents of the present application are excluded, and documents (currently or later attached to the present application) that limit the widest range of the scope of the present application are also excluded. It should be noted that if the description, definition, and/or terms used in the appended application of the present disclosure is inconsistent or conflicting with the content described in the present disclosure, the use of the description, definition and/or terms of the Current disclosure shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:
1. A system, comprising:
at least one storage medium including a set of instructions;
at least one processor in communication with the at least one storage medium, wherein when executing the set of instructions, the at least one processor is configured to cause the system to:
obtain image data and tissue density distribution data;
display the image data and the tissue density distribution data, wherein the tissue density distribution data is displayed in one or more charts outside the displayed image data, the one or more charts including density segmentations, and the displayed image data includes a tissue density analysis region corresponding to the tissue density distribution data;

adjust the tissue density distribution data displayed in the one or more charts by adjusting at least part of the density segmentations;
adjust the image data by adjusting the tissue density analysis region based on the adjusted tissue density distribution data; and
display the adjusted image data and the adjusted tissue density distribution data.

2. The system of claim 1, wherein the tissue density distribution data includes CT values based on the image data.

3. The system of claim 1, wherein to adjust the tissue density distribution data displayed in the one or more charts, the at least one processor is configured to cause the system to:
adjust the at least part of the density segmentations through one or more tissue density segmentation thresholds.

4. The system of claim 3, wherein to adjust one or more tissue density segmentation thresholds, the at least one processor is configured to cause the system to:
modify a tissue density segmentation threshold, add a tissue density segmentation threshold, and/or delete a tissue density segmentation threshold with annotation, mouse input, or voice input.

5. The system of claim 1, wherein the at least one processor is configured to cause the system to:
update the tissue density distribution data in the one or more charts simultaneously according to an adjustment result.

6. The system of claim 5, wherein the at least one processor is configured to cause the system to:
update at least one of a color or statistics data of a same density segmentation in the one or more charts simultaneously according to the adjustment result.

7. The system of claim 1, wherein the one or more charts include at least one of a block diagram, a histogram, or a table.

8. A method for tissue density analysis, comprising:
obtaining image data and tissue density distribution data;
displaying the image data and the tissue density distribution data, wherein the tissue density distribution data is displayed in one or more charts outside the displayed image data, the one or more charts including density segmentations, and the displayed image data includes a tissue density analysis region corresponding to the tissue density distribution data;
adjusting the tissue density distribution data displayed in the one or more charts by adjusting at least part of the density segmentations;
adjusting the image data by adjusting the tissue density analysis region based on the adjusted tissue density distribution data; and
displaying the adjusted image data and the adjusted tissue density distribution data.

9. The method of claim 8, wherein the tissue density distribution data includes CT values based on the image data.

10. The method of claim 8, wherein adjusting the tissue density distribution data displayed in the one or more charts comprises:
adjusting the at least part of the density segmentations through one or more tissue density segmentation thresholds.

11. The method of claim 10, wherein adjusting one or more tissue density segmentation thresholds comprises:
modifying a tissue density segmentation threshold, adding a tissue density segmentation threshold, and/or deleting a tissue density segmentation threshold with annotation, mouse input, or voice input.

12. The method of claim 8, further comprising:
updating the tissue density distribution data in the one or more charts simultaneously according to an adjustment result.

13. The method of claim 12, further comprising:
updating at least one of a color or statistics data of a same density segmentation in the one or more charts simultaneously according to the adjustment result.

14. The method of claim 8, the one or more charts include at least one of a block diagram, a histogram, or a table.

15. A system, comprising:
at least one storage medium including a set of instructions;
at least one processor in communication with the at least one storage medium, wherein when executing the set of instructions, the at least one processor is configured to cause the system to:
obtain image data and tissue density distribution data;
display the tissue density distribution data in one or more color masks on the image data and in one or more charts outside the displayed image data, the one or more charts including density segmentations;
adjust the tissue density distribution data displayed in the one or more color masks by adjusting at least part of the density segmentations; and
display adjusted tissue density distribution data in the one or more color masks and in the one or more charts.

16. The system of claim 15, wherein the tissue density distribution data includes CT values based on the image data.

17. The system of claim 15, wherein to adjust the tissue density distribution data displayed in the one or more color masks, the at least one processor is configured to cause the system to:
adjust the at least part of the density segmentations through one or more tissue density segmentation thresholds.

18. The system of claim 17, wherein to adjust one or more tissue density segmentation thresholds, the at least one processor is configured to cause the system to:
modify a tissue density segmentation threshold, add a tissue density segmentation threshold, and/or delete a tissue density segmentation threshold with annotation, mouse input, or voice input.

19. The system of claim 15, wherein the at least one processor is configured to cause the system to:
update the tissue density distribution data in the one or more color masks simultaneously according to an adjustment result.

20. The system of claim 19, wherein the at least one processor is configured to cause the system to:
update at least one of a color or statistics data of a same density segmentation in the one or more color masks simultaneously according to the adjustment result.

* * * * *